United States Patent [19]

Eaton et al.

[11] Patent Number: 4,701,713
[45] Date of Patent: Oct. 20, 1987

[54] OIL AND FUEL CONTAMINATION MONITORING SYSTEM

[75] Inventors: Favre E. Eaton, Winsted; James F. Brazant, Branford; Lawrence E. Thornton, Simsbury, all of Conn.

[73] Assignee: Combustion Engineering, Inc., Windsor, Conn.

[21] Appl. No.: 683,845

[22] Filed: Dec. 20, 1984

[51] Int. Cl.$^4$ ............................................. G01R 27/22
[52] U.S. Cl. ..................................... 324/442; 324/439
[58] Field of Search ........................ 324/442, 439, 441; 204/406

[56] References Cited

U.S. PATENT DOCUMENTS 3,263,224 7/1966 Berman et al. .................. 324/439 X
4,496,906 1/1985 Clack ..................................... 324/439

*Primary Examiner*—Reinhard J. Eisenzopf
*Assistant Examiner*—Robert W. Mueller
*Attorney, Agent, or Firm*—John H. Mulholland

[57] ABSTRACT

A contamination monitoring system is disclosed wherein a low frequency alternating current signal is applied to a remotely mounted probe in the liquid being monitored for contamination. A fixed resistor located at the probe is electrically in parallel with the resistance of the liquid being monitored. The resistor is isolated from the liquid and allows a signal to be transmitted through an interconnecting cable even though the liquid resistance is very high. A signal is returned to signal processing electronics via the interconnecting cable to a high input impedance amplifier which drives an isolation transformer. The isolated electrical signal induced on the secondary winding of the isolation transformer drives a two stage amplifier circuit the output of which is representative of the amplitude of the isolated electrical signal which in turn is representative of the resistance of a path between the alternating current signal generating means and the high input impedance amplifier that drives the isolation transformer. The representative resistance is applied to three comparator circuits that indicate and alarm the three conditions; (a) an increase in conductivity in a normally nonconductive liquid, (b) an abnormally high conductive condition indicative of a short circuit and (c) unusual increases in nonconductive measurments which would indicate open circuit conditions in the cable.

28 Claims, 4 Drawing Figures

OIL AND FUEL COMTAMINATION MONITORING SYSTEM

BACKGROUND OF THE INVENTION

This invention relates to monitoring oil and fuel for contamination and in particular to a probe for monitoring the level of contamination within a fuel or oil reservoir remotely located from the signal processing electronics and connected thereto by a cable.

Failure of equipment, such as pumps, is often due to contaminants such as water in the bearing lubricating oil. Failure of the bearing would often lead to an investigation into the failure finding that water in the lubricating oil led to increased bearing friction and premature failure. To detect the presence of water in lubricating oil prior to failure of the bearing, samples of bearing lubricant have been removed from a drain port in the lubricant reservoir and analyzed in a laboratory to determine whether the sample lubricant was contaminated.

What is needed is an apparatus for continuously monitoring the lubricating oil to determine when a contaminant reaches a predetermined level in the reservoir. The signal processing portion of such an apparatus would be mounted remotely from the lubricating oil reservoir with a probe mounted in the lubricating oil reservoir such as in the drain port yet retaining the function of the lubricating oil reservoir drain.

SUMMARY OF THE INVENTION

The present invention provides apparatus for detecting and indicating that the level of a contaminant has reached a predetermined level near the drain port of a grounded conductive reservoir containing in its interior a nonconductive fluid, such as lubricating oil or fuel, by detecting the resistance of a path having two parallel branches between a signal generator and earth ground. A known resistance is placed in the first parallel branch. The second parallel branch consists of a probe and the nonconductive fluid such as fuel or oil. A low frequency alternating current signal is generated and passed through the two parallel branches thence through another resistance forming a voltage divider network. The known resistance is physically isolated from the nonconductive fluid and allows the low frequency signal to be transmitted through an interconnecting cable even though the resistance of the nonconductive fluid is high. Furthermore, the signal processing electronics may be remotely located relative to the probe. The voltage at the divided voltage point of the voltage divider network is monitored as indicative of the total resistance of the two parallel branches. The voltage at the divided voltage point varies with the resistance between the probe and the vessel and thus may be used as an indication of the presence or absence of a contaminant bridging between the vessel and the probe. A normal operating condition indicating absence of a contaminant is indicated by a green lamp. The voltage at the voltage divider point is compared to a predetermined set point or set points to determine the presence of abnormalities, and thereupon deenergize the normal operation indicator and energize an abnormality alarm circuit indicator.

DESCRIPTION OF THE PREFERRED EMBODIMENT

Figure 1A:
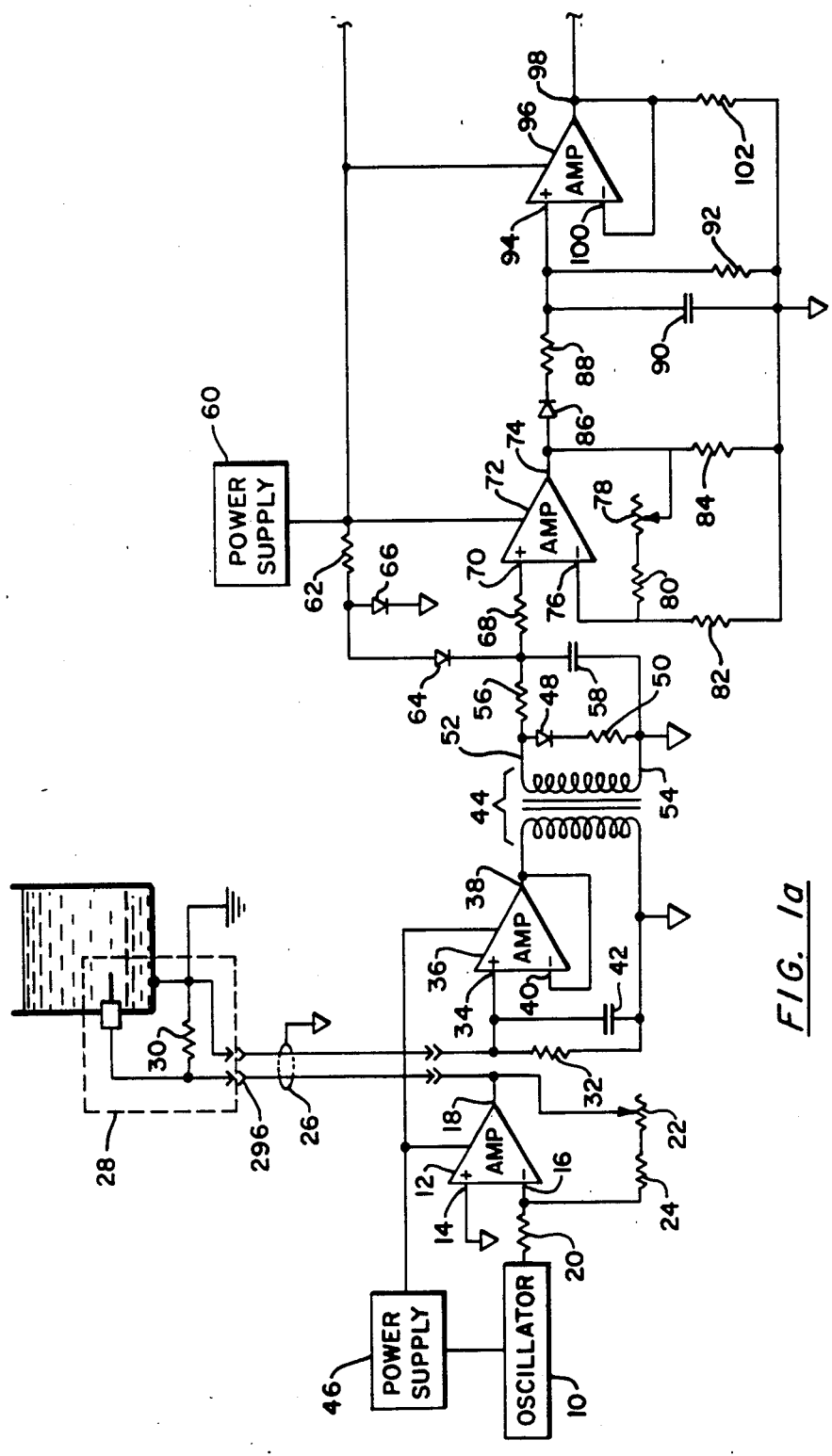
FIGS. 1a and 1b are each portions of the electrical circuit embodying the present invention.
Figure 1B:
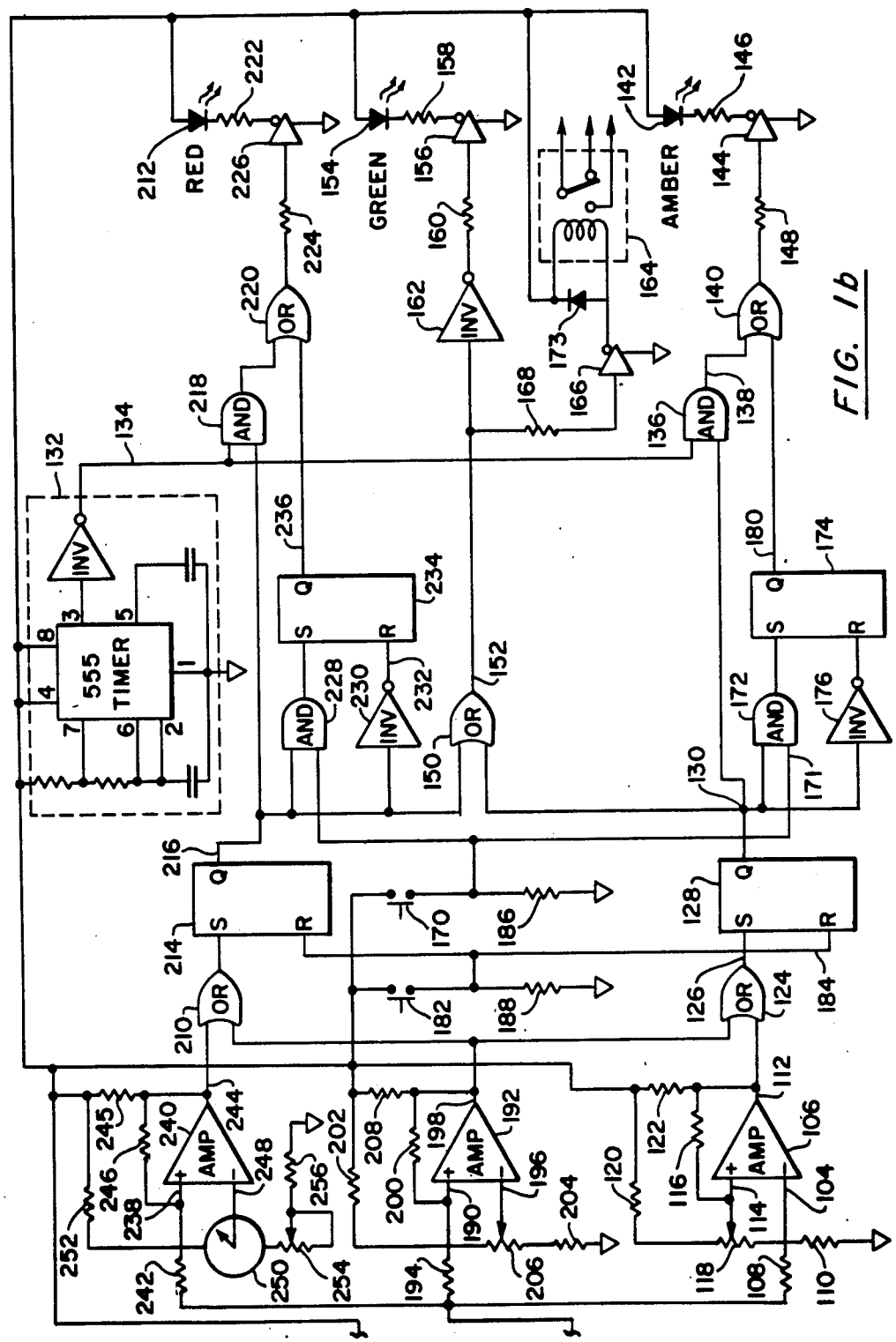

Referring to the drawing, there is depicted therein apparatus for detecting and indicating the resistance of a nonconductive fluid near the drain port of a grounded conductive reservoir containing in its interior in nonconductive fluid designed in accordance with the present invention as best seen schematically in FIG. 1. The values of resistive and capacitive components in the preferred embodiment are listed in Table 1 below.

Oscillator 10 of conventional design provides a low frequency alternating current signal to operational amplifier 12. In the preferred embodiment, the low frequency alternating signal is a sinusoid having a frequency of less than 100 hertz and preferably less than about 50 hertz, but it is understood that other wave shapes such as triangular, saw-tooth or square waves in the same frequency range are contemplated within the scope of the invention. Operational amplifier 12 has a noninverting input terminal 14 grounded to signal ground, and inverting input terminal 16 at which the low frequency oscillator signal is presented and an output terminal 18. Resistor 20 is coupled between oscillator 10 and inverting input terminal 16. A feedback resistance network comprised of potentiometer 22 and resistor 24 couples output terminal 18 to the inverting input terminal 16. Operational amplifier 12 matches the impedance between oscillator 10 and shielded cable 26, and may introduce a gain depending upon the combined resistance of potentiometer 22 and resistor 24 as compared to the resistance of resistor 20. In the preferred embodiment, the operational amplifier 12 provides a gain of approximately three.

Shielded cable 26 conducts the output of operational amplifier 12 to probe assembly 28 and conducts back to the below described signal processing electronics a signal from probe assembly 28. In the preferred embodiment, shielded cable 26 may be up to 2,000 feet in length. At the low frequency of oscillator 10, the capacitance of cable 26 is negligible and does not load the output of amplifier 12. Probe assembly 28 is mounted in the drain port of a nonconductive fluid sump, such as oil, with the probe immersed in the nonconductive fluid. The sump is earth grounded so that when a conductive contaminant accumulates in the lower portion of the sump the resistance of the nonconductive fluid between the probe and the sump changes and a conductive path is formed between the probe and the sump.

Resistor 30, which is an integral part of probe assembly 28, provides a self-test feature. With a circuit completed between oscillator 10 and operational amplifier 36, which may include cable 26, there is a minimum resistance therebetween through which the current should flow. Cessation of the current would indicate an open circuit such as a break in cable 26 or that cable 26 is unplugged from cable connector 296. Resistor 30 is mounted on the probe assembly electrically in parallel with the resistance of the liquid being monitored, that is, in parallel with a path from one conductor of cable 26 through the probe and sump to another conductor of cable 26 to earth ground. The low frequency alternating signal from output terminal 18 is applied to the non-earth ground common point of these two parallel branches. Thus, the low frequency alternating signal provided from output terminal 18 of operational amplifier 12 sees a variable resistance in the parallel branches that is dependent upon whether a contaminant bridges from the probe to the sump or varies the conductivity of a nonconductive fluid between the probe and the sump or whether the probe is insulated from the sump by a nonconductive fluid.

The earth ground common point of these two parallel branches is common to the first end of a resistor 32 through a conductor of shielded cable 26 thereby forming a voltage divider circuit. The second end of resistor 32 is grounded to signal ground. In the preferred embodiment, the ratio of resistor 30 to resistor 32 is 10 to 1.

The divided voltage provides an input to noninverting input terminal 34 of isolation amplifier 36. Isolation amplifier 36 has a high input impedance so as not to attenuate the signal returned from probe assembly 28 via a shielded cable 26. Isolation amplifier 36 also performs impedance matching. The output from isolation amplifier 36, output terminal 38 is fed back to inverting input terminal 40 of isolation amplifier 36. A small capacitor 42 is coupled between noninverting input terminal 34 and signal ground to suppress noise.

Output terminal 38 of isolation amplifier 36 is coupled to a signal grounded primary of isolation transformer 44. Isolation transformer 44 electrically isolates the voltage signal induced in the secondary winding of isolation transformer 44 from the electrical circuit containing oscillator 10. To maintain complete electrical isolation, oscillator 10, operational amplifier 12 and isolation amplifier 36 are powered by power supply 46 which is independent from power supply 60 providing power to the remainder of the signal processing electronics described below. Power supplies 46 and 60 are of conventional design.

The isolated electrical signal induced in the secondary winding of isolation transformer 44 is indicative of the resistance of a path between oscillator 10 and noninverting input terminal 34 of isolation amplifier 36. The major resistances influencing the path resistance are resistance 30 and the fluid resistance between the probe and sump. The induced voltage in the secondary winding of isolation transformer 44 is indicative of the voltage at the voltage divider point, that is the voltage at noninverting input terminal 34 of operational amplifier 36. This voltage is nonlinear and may be used for useful information regarding the resistivity of the nonconductive fluid and whether shielded cable 26 is electrically connected to probe assembly 28.

The isolated electrical signal induced in the secondary winding of isolation transformer 44 is, in the preferred embodiment, a low frequency full wave sinusoid. A series diode-resistor network comprised of diode 48 and resistor 50 is coupled between leads 52 and 54 of the secondary winding of isolation transformer 44. The lead common to resistor 50 is grounded to signal ground. A series resistor-capacitor network is coupled across diode 48 and resistor 50 in parallel therewith. Resistor 56 has a first lead in common with the anode of diode 48 and lead 52 of transformer 44. Capacitor 58 connects between the second lead of resistor 56 and grounded lead 54 of transformer 44.

Power supply 60 which provides power to the signal processing electronics described below is connected through resistor 62 and diode 64 to the common point between resistor 56 and capacitor 58. The anode of diode 64 is connected through diode 66 to signal ground. Resistor 68 couples the cathode of diode 64 to the noninverting input terminal 70 of operational amplifier 72.

The above-described network comprises a halfwave rectifier that provides the positive half of the sinusoid to noninverting input terminal 70. During the positive half of each sinusoid, diode 64 blocks preventing the signal from passing back through power supply 60 to ground. The halfwave rectified isolated electrical signal is presented to noninverting input terminal 70 of operational amplifier 72 through resistors 56 and 68. Capacitor 58 provides a path to ground for any noise imposed on the halfwave rectified isolated electrical signal. During the negative half of the cycle, diode 48 blocks preventing the signal from reaching noninverting input terminal 70 and current passes from power supply 60 through resistor 62, diode 64, resistor 56, diode 48 and resistor 52 to signal ground.

With the cathode of diode 66 connected to signal ground, the anode of diode 56 remains one diode voltage drop above signal ground. Thus, the cathode of diode 64 which is the common point to resistor 56, capacitor 58, resistor 68 and diode 64 remains essentially at signal ground.

Operational amplifier 72 may be a conventional operational amplifier having high input impedance and low output impedance to provide impedance matching between the nondistorting halfwave rectifier circuit described above and a hold circuit described below.

Output terminal 74 of operational amplifier 72 is coupled to inverting input terminal 76 of operational amplifier 72 through the series network comprised of potentiometer 78 and resistor 80. The feedback so provided maintains the gain of operational amplifier 72 at approximately unity. Inverting input terminal 76 is coupled to signal ground through resistor 82; output terminal 74 is coupled to signal ground through resistor 84.

The hold circuit is comprised of diode 86, resistor 88, capacitor 90 and resistor 92. Output terminal 74 is connected to the anode of diode 86 thence through the series combination of resistors 88 and capacitor 90 to signal ground. Resistor 92 is coupled between the common point of resistor 88 and capacitor 90 and signal ground such that resistor 92 is electrically in parallel with capacitor 90. In this manner, the hold circuit charges capacitor 90 to the maximum value of voltage at output terminal 74 less one diode voltage drop. Diode 86 prevents capacitor 90 from discharging back through resistor 88 and resistor 84 to signal ground. Resistor 92 is a large resistance and provides a path to signal ground that in combination with capacitor 90 has a large time constant to discharge capacitor 90 when the voltage at output terminal 74 is decreasing. The common point between resistor 88, capacitor 90 and resistor 92 is coupled to the noninverting input terminal 94 of operational amplifier 96. Operational amplifier 96 has a high input impedance, so as not to load the hold circuit, and a low output impedance. The output from operational amplifier 96 is coupled from output terminal 98 to inverting input terminal 100 such that the gain of operational amplifier 96 is unity. Resistor 102 is coupled between output terminal 98 and signal ground to load the output of operational amplifier 96. The output of operational amplifier 96 is a nonlinear DC voltage signal indicative of the resistance or alternatively the conductance between oscillator 10 and the divided voltage point.

The voltage signal presented at output terminal 98 of operational amplifier 96 is presented as the input to three comparator circuits. The comparator circuits drive an alarm relay and three light emitting diodes to indicate the current operating status of the contamination monitoring system. Under normal operating conditions a green light emitting diode is energized continuously and the alarm relay as well as a red and an amber light emitting diodes are deenergized. Under abnormal operating conditions, the green light emitting diode is deenergized, the alarm relay is energized, and a red light emitting diode is energized when a low resistance compared to a predetermined variable resistance exists between the probe and sump, or an amber light emitting diode is energized to indicate that an abnormally low resistance, for example, lower than water contamination, exists as the combined resistance of resistor 30 and the resistance of the liquid being monitored indicating inter alia a broken or disconnected cable 26, or both the red and amber light emitting diodes are energized indicating that an abnormally high conductance is detected or a shorted condition exists at the probe. The red and amber light emitting diodes either individually or in combination are operated in a flashing mode upon initially detecting an abnormal operating condition. Upon operator acknowledgment the red and amber light emitting diodes remain energized steadily, that is in a nonflashing mode, until the condition initiating their operation is cleared and an operator presses a reset or clear switch.

The output signal from operational amplifier 96 is coupled to the inverting input terminal 104 of operational amplifier 106 through resistor 108. The output from operational amplifier 106 presented at output terminal 112 is coupled to noninverting input terminal 114 through feedback resistor 116. Noninverting input terminal 114 is also coupled to power supply 60 through the divided voltage point of potentiometer 118 and resistor 120 in series therewith. Potentiometer 118 is coupled to signal ground through resistor 110. Output terminal 112 of operational amplifier 106 is also coupled to power supply 60 through resistor 122.

The resistive network comprised of resistors 110 and 120 as well as potentiometer 118 when coupled to power supply 60 provide a voltage divider network which in turn provides a voltage to noninverting input terminal 114 of operational amplifier 106 representing a predetermined path resistance set point to which the output of operational amplifier 96 is compared to detect an abnormally low isolated electrical signal. An abnormally low isolated electrical signal indicates lower than usual conductivity and that the shielded cable 26 has been cut or probe assembly 28 has been disconnected from cable 26 and not reconnected. An abnormally high isolated electrical signal indicates that the combined resistance through the two parallel resistive paths is low.

Potentiometer 118 establishes a variable predetermined path resistance set point that is compared to the isolated electrical signal. The variable predetermined path resistance set point established by potentiometer 118 is set just greater than the resistance of resistor 30. Since resistance 30 is in parallel with the resistance of the nonconductive fluid being contamination monitored, the combined parallel resistance never exceeds the value of resistance 30. Thus, when the isolated electrical signal is unusually low indicating a combined parallel resistance greater than that of resistor 30, the oscillator output is not being detected at the divided voltage point for such reasons as cable 26 is cut or disconnected from probe assembly 28.

When the isolated electrical signal goes low relative to the predetermined path resistance set point, the output of operational amplifier 106 goes from zero volts to the voltage level of power supply 60 which is compatible with the digital electronics of the signal processing circuitry. The output of operational amplifier 106 is one of two inputs to OR gate 124. When either input to OR gate 124 goes high, output 126 of OR gate 124 goes high setting alarm latch 128 thereby causing output 130 of alarm latch 128 to go high.

Oscillator 132 in the preferred embodiment is of conventional design having a frequency of 4 hertz and duty cycle of 80%. Oscillator 132 shown as being constructed utilizing a 555 timer operating in an astable multivibrator node. Output 134 from oscillator 132 is combined in AND gate 136 with output 130 from alarm latch 128. Output 138 from AND gate 136 is one of two inputs to OR gate 140. When either of the inputs to OR gate 140 are high, amber LED 142 is energized through LED driver 144 and current limiting resistors 146 and 148. Thus, for the duration of output 130 being high and the second input to OR gate 140 being low, oscillator 132 will energize amber LED 142 in a flashing mode.

Output 130 is one of two inputs to OR gate 150. When either input to OR gate 150 goes high, the output 152 of OR gate 150 goes high. Concomitantly, with output 152 going high, green LED 154 is deenergized by LED driver 156 and current limiting resistors 158 and 160 as the output of inverter 162 goes low. Output 152 going high also energizes alarm relay 164 through driver 166 and resistor 168. Diode 173 across the coil of alarm relay 164 dissipates the energy stored therein upon deenergizing alarm relay 164. In this manner, green LED 154 is deenergized and alarm relay 164 is energized anytime amber LED 142 is energized.

An operator may acknowledge the flashing amber LED 142 by depressing acknowledgment switch 170 thereby applying the voltage level of power supply 60 to one input of AND gate 172. Output 130 provides the second input to AND gate 172 such that when acknowledgment switch 170 is depressed and output 130 is high the output of AND gate 172 goes high setting acknowledgment latch 174. Output 130 is inverted in inverter 176 providing an inverted signal 130 to the reset input of acknowledgment latch 174. Thus, with the presence of output signal 130 and operator actuation of acknowledgment switch 170, acknowledgment latch 174 is set providing a high output 180 that is the second input to OR gate 140. The continuously high output 180 overrides the intermittently high output 138 to provide a continuous high output from OR gate 140 to drive amber LED 142 continuously in a nonflashing mode upon operator actuation of acknowledgment switch 170.

Amber LED 142 remains energized until the condition causing its initiation is removed and the operator subsequently actuates clear switch 182 which applies the voltage level of power supply 60 to reset terminal 184 of alarm latch 128 thereby causing output 130 to go low which in turn causes output 138 to go low and acknowledgment latch 174 to reset causing output 180 to go low and thereby deenergizing the amber LED 142. Output 130 going low causes output 152 of OR gate 150 to go low when the second input to OR gate 150 (output 216) is low deenergizing the alarm relay 164 and energizing green LED 154.

Resistors 186 and 188 perform a similar function. Resistor 186 ties input 171 of AND gate 172 to signal ground when acknowledgment switch 170 is not actuated. Resistor 188 ties reset input 184 of alarm latch 128 to signal ground when clear switch 182 is not actuated.

Output 98 from operational amplifier 96 is coupled to the noninverting input terminal 190 of operational amplifier 192 through resistance 194. The comparator includes operational amplifier 192 having noninverting input terminal 190, inverting input terminal 196 and an output terminal 198. Output terminal 198 is coupled to the noninverting input terminal 190 through feedback resistance 200. A signal representing a predetermined path resistance set point is provided to inverting input terminal 196 through a resistance network connected between power supply 60 and signal ground. The resistance network is comprised of resistors 202 and 204 and potentiometer 206. The divided voltage point of potentiometer 206 is coupled to inverting input terminal 196 providing a signal representing a predetermined variable resistance set point that is dependent upon the liquid being monitored and the desired conductivity level at which an alarm should energize. The variable predetermined path resistance set point established by potentiometer 206 is set to represent a lower resistance than is set on resistance 250 so as to indicate an unusually low resistance, lower than just normal contamination, such as a direct short between the probe and tank. The incoming electrically isolated signal, output 98 from operational amplifier 96, is compared to the variable predetermined set point and when the isolated electrical signal is greater than the predetermined set point, the output of operational amplifier 192 goes high making a transition from zero volts to the voltage level of power supply 60. Output 192 going high indicates that an abnormally conductive measurement is detected or a shorted condition exists between the probe and sump.

Resistor 208 is coupled between output terminal 198 and power supply 60. The output from operational amplifier 192 presented at output terminal 198 is the second input to OR gate 124. When the output of operational amplifier 192 goes high, the output of OR gate 124 also goes high causing amber LED to operate in a flashing mode as described above. The output from operational amplifier 192 also provides one of the two inputs to OR gate 210 which energizes red LED 212 in a flashing mode similarly to the output of OR gate 124 energizing amber LED 142 in a flashing mode. Thus, when output 198 of operational amplifier 192 goes high indicating that the isolated electrical signal is greater than the predetermined set point established by the voltage divider network of resistors 202 and 204 as well as potentiometer 206 connected between power supply 60 and signal ground, both red LED 212 and amber LED 142 operate in a flashing mode.

When the output of OR gate 210 goes high, alarm latch 214 is set. Output 216 from alarm latch 214 goes high and when combined with the output 134 from oscillator 132 in AND gate 218 provides an alternating high then low input to OR gate 220 that energizes red LED 212 in a flashing mode by alternately energizing then deenergizing red LED 212 at the frequency rate of oscillator 132 through current limiting resistors 222 and 224 and LED driver 226. Thus, when the resistance between oscillator 10 and the noninverting input terminal 34 of operational amplifier 36 is abnormally low compared to a variable predetermined set point signal established by potentiometer 206, both red LED 212 and amber LED 142 are energized in a flashing mode. Concomitantly, as described above, green LED 154 is deenergized and alarm relay 164 is energized.

The acknowledgment switch 170 and control switch 182 functions operate on red LED 212 simultaneously with operating on amber LED 142. Output 216 from alarm latch 214 provides one of two inputs to AND gate 228, output 216 also provides the second input to OR gate 150 to deenergize green LED 154 and energize alarm relay 164 in the above-described manner upon energizing red LED 212. Output 216 is inverted in inverter 230 with the inverted output connected to reset terminal 232 of acknowledgment latch 234. Thus, with red LED 212 operating in a flashing mode, operator actuation of acknowledgment switch 170 applies the voltage of power supply 60 to the second input of AND gate 228 causing the output of AND gate 228 to go high setting acknowledgment latch 234. Setting acknowledgment latch 234 causes output 236 to go high. The continuously high output 236 of acknowledgment latch 234 overrides the intermittently high output of AND gate 238 such that the output of OR gate 220 remains high thereby energizing red LED 212 in a constant, nonflashing mode. Red LED 212 remains energized in a nonflashing mode until the condition that caused output 192 to go high is removed and subsequently the operator actuates clear switch 182 which resets alarm latch 214 causing output 216 to go low, red LED 212 to deenergize, relay 164 to deenergize and green LED 154 to energize.

Thus, when output 198 goes high green LED 152 is deenergized and simultaneously red LED 212 and amber LED 142 are energized in a flashing mode until acknowledged by operator actuation of acknowledgment switch 170 which simultaneously causes red LED 212 and amber LED 142 to operate in a nonflashing mode until subsequently the condition that caused output 198 to go high is removed and clear switch 182 is operator actuated causing alarm latches 214 and 128 to reset.

Output 98 from operational amplifier 96 is provided to the noninverting input terminal 238 of operational amplifier 240 through resistance 242. Operational amplifier 240 has an output presented at output 244. Output 244 is coupled to noninverting input terminal 238 through feedback resistance 246. Output 244 is also coupled to power supply 60 through resistor 245. A variable predetermined set point is coupled to inverting input terminal 248 through a resistor network coupled between power supply 60 and signal ground. Included in the resistor network is a variable resistance 250 shown in more detail in FIG. 2 and discussed in more detail below. The resistance network is comprised of resistor 252, variable resistance 250, potentiometer 254 and resistor 256.

Variable resistance 250 provides a voltage signal representing the desired resistance between oscillator 10 and input terminal 34 of operational amplifier 36 at which an alarm should energize to inverted input terminal 248 that is compared to the isolated electrical signal representing the path resistance between oscillator 10 and input terminal 34 of operational amplifier 36. The desired resistance between oscillator 10 and input terminal 34 of operational amplifier 36 at which an alarm is energized is greater than the variable predetermined path resistance set point established by potentiometer 206, is dependent on the liquid being monitored and the desired conductivity level at which an alarm should energize. When the isolated electrical signal at noninverting input terminal 238 of operational amplifier 240 exceeds the variable preset voltage on inverted input terminal 248 of operational amplifier 240 the resistance between oscillator 10 and noninverting input terminal 34 of operational amplifier 36 is below the desired resistance value as set on variable resistance 250 and the output of operational amplifier 240 goes high causing the output of OR gate 210 to go high setting alarm latch 214, energizing only red LED 212 with a flashing mode, deenergizing green LED 154 and energizing alarm relay 164. Thus, when the conductivity of the fluid being monitored reaches a level set by the divided voltage point of variable resistance 250, output 244 goes high.

Acknowledgment switch 170 may be operator actuated to cause red LED 212 to operate in a continuously energized mode as described above. Subsequent to the removal of the condition that caused the output of operational amplifier 240 to go high, which means to go to the voltage level of power supply 60, clear switch 182 may be operator actuated to deenergize red LED 212, deenergize alarm relay 164 and simultaneously energize green LED 154.

TABLE 1

| COMPONENT REFERENCE NUMERAL THOUSANDS OF OHMS | COMPONENT VALUE IN PREFERRED EMBODIMENT: RESISTANCE IN CAPACITANCE IN MICROFARADS |
| --- | --- |
| 20 | 10 |
| 22 | 10 |
| 24 | 30 |
| 30 | 20 |
| 32 | 2 |
| 42 | .002 |
| 50 | 47 |
| 56 | 47 |
| 58 | .002 |
| 62 | 10 |
| 68 | 3.3 |
| 78 | 10 |
| 80 | 4.3 |
| 82 | 49.9 |
| 84 | 10 |
| 88 | 1 |
| 90 | 10 |
| 92 | 1000 |
| 102 | 1 |
| 108 | 10 |
| 110 | .5 |
| 116 | 10,000 |
| 118 | 2 |
| 120 | 9.53 |
| 122 | 15 |
| 146 | .82 |
| 148 | 10 |
| 158 | .82 |
| 160 | 10 |
| 168 | 10 |
| 186 | 10 |
| 188 | 10 |
| 194 | 10 |
| 200 | 10,000 |
| 202 | 1.67 |
| 204 | 8.25 |
| 206 | 2 |
| 208 | 15 |
| 222 | .820 |
| 224 | 10 |
| 242 | 10 |
| 245 | 15 |
| 246 | 10,000 |
| 250 | See FIG. 2 |
| 252 | 4.75 |
| 254 | 2 |
| 256 | 1 |

Figure 2:
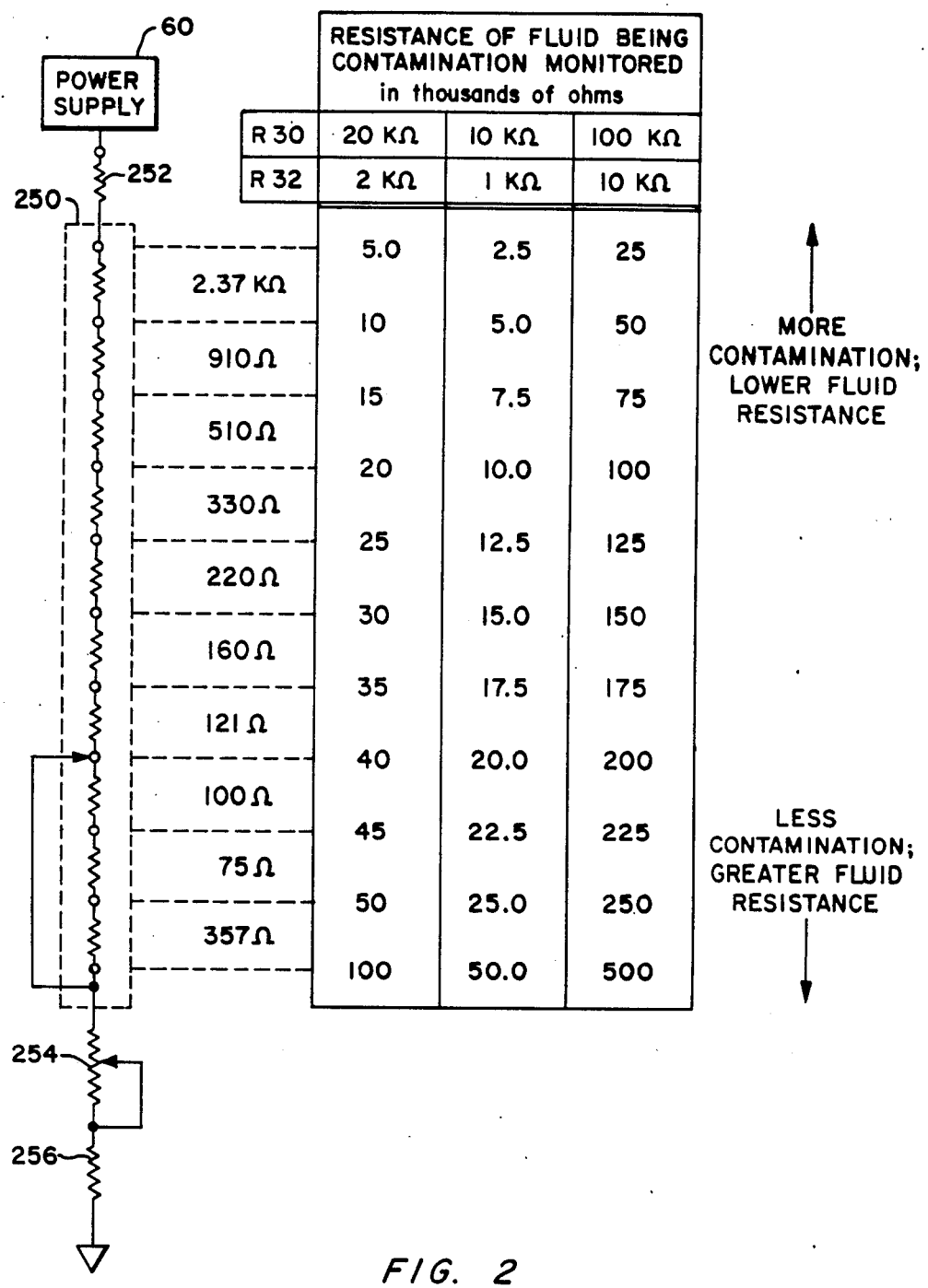
FIG. 2 is a schematic illustration of a variable resistance from FIG. 1b in more detail.

Resistance 250 is a variable resistance as best seen in FIG. 2 wherein the entire voltage divider network between power supply 60 and signal ground is reproduced. The same variable resistance 250 may be used to monitor the contamination of various fluids with differing uncontaminated resistance by using different magnitude resistors 30 and 32. As stated above, in the preferred embodiment the ratio of resistor 30 to resistor 32 is 10 to 1, however, the invention is not limited thereto. The resistance of the fluid being contamination monitored is shown for each setting of variable resistance 250 for three combinations of resistors 30 and 32, each combination having a ratio of 10 to 1 as in the preferred embodiment. The magnitudes of resistors 30 and 32 are not limited to only the values set forth. The resistance values in variable resistance 250 are calculated to provide a curve corresponding to nonlinear output 98 of operational amplifier 96 to provide desired voltage levels corresponding to the conductivity of the fluid being monitored at each break point as inputs to inverted input terminal 248 of operational amplifier 240.

Thus, the green LED is energized in a steady on condition under normal operating conditions, any abnormal operating condition deenergizes green LED 154 and energizes alarm relay 164. Three possible abnormal operating conditions are detectable. When the resistance of the liquid reaches the magnitude set by the divided voltage point of variable resistance 250 red LED 212 is energized. Amber LED 142 is energized to indicate at an abnormally high resistance exists such as a broken or disconnected cable. The third possible indicated condition is when both red LED 212 and amber LED 142 are energized. Under these conditions an abnormally low resistance, for example a resistance lower than that of water contamination exists and it is likely that the probe is touching the tank. Under all operating conditions, alarm latches 128 and 214 maintain the appropriate light emitting diode or diodes energized until the condition causing the alarm is removed.

Figure 3:
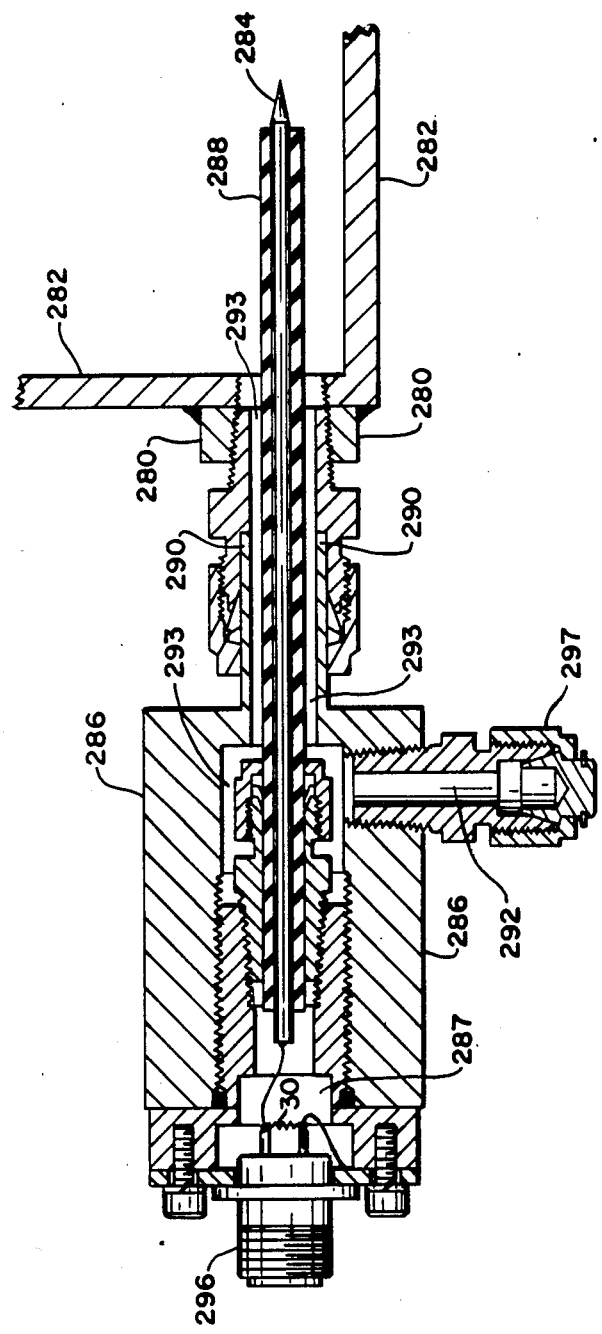
FIG. 3 is a side view partly in section of the probe assembly.

Probe assembly 28, shown in detail in FIG. 3, is designed to be mounted in the drain port of a sump yet retain the drain feature and therefore is shown threaded into threaded coupling 280 integral with tank 282. Probe assembly 28 has electrode 284 extending through housing 286 into tank 282 where electrode 284 is immersed in the nonconductive fluid. Electrode 284 is insulated from housing 286 and tank 282 by insulation 288 that surrounds electrode 284 substantially throughout its length except the tip within tank 282. Surrounding insulation 288 and extending through threaded coupling 280 and tubular extension 290 of housing 286 and into drain means 292 is annular fluid passage 293 that permits fluid to pass from tank 282 to drain means 292 for removal of contaminated nonconductive fluid from tank 282. Drain means 292 is oriented downward so that fluid may be drained from tank 282 when valve means 297 is opened. Maintaining valve means 297 closed prevents nonconductive fluid from draining from tank 282. In this manner, although probe assembly 28 is mounted in the drain port of tank 282, since the diameter of electrode 284 as surrounded by insulation 288 is small relative to the diameter of the drain port, the ability to drain contaminated nonconductive fluid from tank 282 remains. Annular fluid passage 293 terminates beyond drain means 292 with electrode 284 as surrounded by insulation 288 sealed to housing 286 to prevent the nonconductive fluid within tank 282 and annular passage 293 from passing into cavity 287 housing resistor 30. Resistor 30 is an integral part of probe assembly 28 and as shown is mounted internal to cavity 287.

The low frequency alternating current signal generated by oscillator 10 is conducted to probe assembly 28 on shielded cable 26. With cable 26 connected to cable connector 296, the low frequency alternating current signal of oscillator 10 is applied to the parallel branches of resistor 30 and the resistive path through electrode 284 and the nonconductive fluid being contamination monitored to earth grounded tank 282, thence back through cable 26 to the above-described, remotely located signal processing electronics. Thus, should cable 26 not be connected to cable connector 296 or if cable 26 is broken, no return signal is provided to the signal processing electronics.

We claim:

1. A contamination monitoring system for detecting and indicating the resistance of a nonconductive fluid near a drain port of an earth grounded conductive reservoir, comprising:
   a. means for generating an alternating current signal;
   b. probe means adapted to be mounted in a drain port of the reservoir for applying the alternating current signal to the nonconductive fluid, said probe means having
      (i) an electrically conductive electrode extending into and electrically insulated from the earth grounded reservoir, the electrode immersed in the nonconductive fluid and having the alternating current signal applied thereto,
      (ii) a housing having a fluid passage in fluid communication with the reservoir for passing fluid therefrom,
      (iii) closure means in the fluid passage for permitting fluid passage therethrough when opened and preventing fluid passage therethrough when closed, and
      (iv) a first resistance electrically in parallel with the path from the alternating current generating means through the nonconductive fluid to earth ground;
   c. voltage divider means connected between the signal generating means and signal ground for providing a divided voltage point, comprised of the first resistance in parallel with the probe means, said voltage divider means also having a second resistance in series with the first resistance, a first end of the second resistance connected at the divided voltage point to the first resistor and earth ground and a second end of the second resistor connected to signal ground;
   d. voltage detection means connected to the divided voltage point for manifesting a detected voltage signal at the divided voltage point;
   e. isolation means for electrically isolating the detected voltage signal from the electrical circuit containing the alternating current signal generating means resulting in an isolated electrical signal indicative of the resistance of a path between the alternating current signal generating means and the divided voltage point;
   f. means for evaluating the isolated electrical signal to determine the resistance of a path between the alternating current signal generating means and the divided voltage point, thereby determining the degree of conductive contamination in the nonconductive fluids;
   g. means for comparing the path resistance to a predetermined path resistance set point resulting in a compared path resistance signal;
   h. means for indicating normal contamination levels when the path resistance is greater than the predetermined path resistance set point; and
   i. means for indicating abnormal contamination levels when the path resistance is less than the predetermined path resistance set point.

2. Apparatus as recited in claim 1 further comprising cable means interposed between the alternating current signal generating means and the probe means for conducting the alternating current signal to the probe means and for conducting a voltage signal therefrom back to the divided voltage point whereby the probe means may be remotely mounted.

3. Apparatus as recited in claim 1 wherein the alternating current signal is sinusoidal.

4. Apparatus as recited in claim 1 wherein the frequency of the alternating current signal is less than about 50 hertz.

5. Apparatus as recited in claim 1 wherein the comparing means for comparing the path resistance to the predetermined path resistance set point is an operational amplifier.

6. Apparatus as recited in claim 1 further comprising latch means for maintaining in an energized state one of the indicating means upon the occurrence of the condition initiating indication.

7. A contamination monitoring system for detecting and indicating the resistance of a nonconductive fluid near a drain port of an earth grounded conductive reservoir, comprising:
   a. means for generating an alternating current signal;
   b. probe means adapted to be mounted in a drain port of the reservoir for applying the alternating current signal to the nonconductive fluid, said probe means having
      (i) an electrically conductive electrode extending into and electrically insulated from the earth grounded reservoir, the electrode immersed in the nonconductive fluid and having the alternating current signal applied thereto,
      (ii) a housing having a fluid passage in fluid communication with the reservoir for passing fluid therefrom,
      (iii) closure means in the fluid passage for permitting fluid passage therethrough when opened and preventing fluid passage therethrough when closed, and
      (iv) a first resistance electrically in parallel with the path from the alternating current generating means through the nonconductive fluid to earth ground;

c. voltage divider means connected between the signal generating means and signal ground for providing a divided voltage point, comprised of the first resistance in parallel with the probe means, said voltage divider means also having a second resistance in series with the first resistance, a first end of the second resistance connected at the divided voltage point to the first resistor and earth ground and a second end of the second resistor connected to signal ground;

d. voltage detection means connected to the divided voltage point for manifesting a detected voltage signal at the divided voltage point;

e. isolation means for electrically isolating the detected voltage signal from the electrical circuit containing the alternating current signal generating means resulting in an isolated electrical signal indicative of the resistance of a path between the alternating current signal generating means and the divided voltage point;

f. means for comparing the isolated electrical signal to a predetermined path resistance set point, the comparing means having a first input port for receiving the isolated electrical signal, a second input port for receiving the predetermined path resistance set point and an output port at which a compared path resistance signal is presented; and g. means for responsive to the compared path resistance signal for indicating that the resistance of a path between the alternating current generating means and the divided voltage point is less than the predetermined path resistance set point upon the isolated electrical signal increasing to be greater than the predetermined path resistance set point.

8. Apparatus as recited in claim 7 further comprising cable means interposed between the alternating current signal generating means and the probe means for conducting the alternating current signal to the probe means and for conducting a voltage signal therefrom back to the divided voltage point whereby the probe means may be remotely mounted.

9. Apparatus as recited in claim 7 wherein comparing means for comparing the isolated electrical signal to a predetermined path resistance set point is an operational amplifier.

10. Apparatus as recited in claim 7 further comprising latch means for maintaining in an energized state the indicating means upon the occurrence of the condition initiating indication.

11. A contamination monitoring system for detecting and indicating the resistance of a nonconductive fluid near a drain port of an earth grounded conductive reservoir, comprising:

a. means for generating an alternating current signal;

b. probe means adapted to be mounted in a drain port of the reservoir for applying the alternating current signal to the nonconductive fluid, said probe means having (i) an electrically conductive electrode extending into and electrically insulated from the earth grounded reservoir, the electrode immersed in the nonconductive fluid and having the alternating current signal applied thereto, (ii) a housing having a fluid passage in fluid communication with the reservoir for passing fluid therefrom, (iii) closure means in the fluid passage for permitting fluid passage therethrough when opened and preventing fluid passage therethrough when closed, and (iv) a first resistance electrically in parallel with the path from the alternating current generating means through the nonconductive fluid to earth ground;

c. voltage divider means connected between the signal generating means and signal ground for providing a divided voltage point, comprised of the first resistance in parallel with the probe means, said voltage divider means also having a second resistance in series with the first resistance, a first end of the second resistance connected at the divided voltage point to the first resistor and earth ground and a second end of the second resistor connected to signal ground;

d. voltage detection means connected to the divided voltage point for manifesting a detected voltage signal at the divided voltage point;

e. isolation means for electrically isolating the detected voltage signal from the electrical circuit containing the alternating current signal generating means resulting in an isolated electrical signal indicative of the resistance of a path between the alternating current signal generating means and the divided voltage point;

f. means for comparing the isolated electrical signal to a first predetermined path resistance set point, the comparing means having a first input port for receiving the isolated electrical signal, a second input port for receiving a first predetermined path resistance set point and an output port at which the first compared resistance signal is presented;

g. means responsive to the first compared path resistance signal for indicating that the resistance of a path between the alternating current signal generating means and the divided voltage point is less than the first predetermined path resistance set point upon the isolated electrical signal increasing to be greater than the first predetermined path resistance set point;

h. means for comparing the isolated electrical signal to a second predetermined path resistance set point, the comparing means having a first input port for receiving the isolated electrical signal, a second input port for receiving a second predetermined path resistance set point, the second predetermined path resistance set point, the second predetermined path resistance set point being greater than the first predetermined path resistance set point, and an output port at which a second compared path resistance signal is presented; and i. means responsive to the second compared path resistance signal for indicating that the resistance of a path between the alternating current signal generating means and the divided voltage point is greater than the second predetermined path resistance set point upon the isolated electrical signal decreasing to be less than the second predetermined path resistance set point.

12. Apparatus as recited in claim 11 further comprising cable means interposed between the alternating current signal generating means and the probe means for conducting the alternating current signal to the probe means and for conducting a voltage signal therefrom back to the divided voltage point whereby the probe means may be remotely mounted.

13. Apparatus as recited in claim 11 wherein the comparing means for comparing the isolated electrical signal to a predetermined parallel path resistance set point is an operational amplifier.

14. Apparatus as recited in claim 11 further comprising latch means for maintaining in an energized state one of the indicating means upon the occurrence of the condition initiating indication.

15. Apparatus as recited in claim 11 further comprising oscillator means for periodically turning on then off an indicating means upon the occurrence of the condition initiating indication.

16. Apparatus as recited in claim 11 wherein the isolation means is a transformer having the detected voltage applied to the primary winding thereof thereby inducing the isolated electrical signal on the inductively coupled secondary winding thereof.

17. Apparatus as recited in claim 11 wherein the voltage detection means is an operational amplifier having a high input impedance that provides an operational amplifier output that is the detected voltage signal.

18. Apparatus as recited in claim 11 wherein the ratio of magnitudes of the first resistance to the second resistance is 10 to 1.

19. Apparatus as recited in claim 11 wherein a predetermined path resistance set point is adjustable.

20. Apparatus for detecting and indicating that a level of a conductive contaminant has reached a predetermined level near the drain port of a grounded conductive reservoir containing in its interior a nonconductive fluid, comprising:
   (a) means for generating an alternating current signal;
   (b) probe means extending into and electrically insulated from the earth grounded reservoir having the alternating current signal applied thereto, said probe means having a housing having a fluid passage in fluid communication with the reservoir for passing fluid therefrom, said probe means having a closure means in the fluid passage for permitting fluid passage therethrough when opened and preventing fluid passage therethrough when closed, said probe means adapted to be mounted in the drain port of the reservoir to detect that the level of contaminant has reached the level of the probe means;
   (c) voltage divider means connected between the signal generating means and signal ground, having a first resistance connected between the signal generating means and earth ground such that the first resistance is in parallel with the probe means and having a second resistance in series with the first resistance, a first end of the second resistance connected at a divided voltage point to the first resistor and earth ground and a second end of the second resistor connected to signal ground;
   (d) voltage detection means connected to the divided voltage point to manifest the voltage signal at the divided voltage point;
   (e) isolation means for electrically isolating the detected voltage signal at the divided voltage point from the electrical circuit containing the alternating current signal generating means resulting in an isolated electrical signal indicative of the resistance of a path between the alternating current signal means and the divided voltage point;
   (f) means for comparing the isolated electrical signal to a first predetermined path resistance set point, the comparing means having a first input port for receiving the isolated electrical signal, a second input port for receiving a first predetermined path resistance set point and an output portat which a first compared path resistance signal is presented;
   (g) means responsive to the first compared path resistance signal for indicating that the resistance of a path between the probe means and the vessel is less than the first predetermined path resistance upon the isolated electrical signal decreasing to be less than the first predetermined path resistance set point;
   (h) means for comparing the isolated electrical signal to a second predetermined path resistance set point, the comparing means having a first input port for receiving the isolated electrical signal, a second input port for receiving a second predetermined path resistance set point, the second predetermined path resistance set point being less than the first predetermined path resistance set point, and an output port at which a second compared path resistance signal is presented;
   (i) means responsive to the second compared path resistance signal for indicating that the resistance of a path between the probe means and the vessel is less than the second predetermined path resistance upon the isolated electrical signal decreasing to be less than the second predetermined path resistance set point;
   (j) means for comparing the isolated electrical signal to a third predetermined path resistance set point, the comparing means having a first input port for receiving the isolated electrical signal, a second input port for receiving the third predetermined path resistance set point, the third predetermined path resistance set point being greater than the first predetermined path resistance set point, and an output port at which a third compared path resistance signal is presented; and
   (k) means responsive to the third compared path resistance signal for indicating that the resistance of a path between the alternating current signal generating means and the divided voltage point is less than the third resistance set point upon the isolated electrical signal increasing to be greater than the third predetermined path resistance set point.

21. Apparatus as recited in claim 20 further comprising cable means interposed between the alternating current signal generating means and the probe means for conducting the alternating current signal to the probe means and for conducting the voltage signal therefrom back to the divided voltage point, whereby the probe means may be remotely mounted.

22. Apparatus as recited in claim 20 wherein the comparing means for comparing the isolated electrical signal to a predetermined path resistance set point is an operational amplifier.

23. Apparatus as recited in claim 20 further comprising latch means for maintaining in an energized state one of the indicating means upon the occurrence of the condition initiating indication.

24. Apparatus as recited in claim 20 further comprising oscillator means for periodically turning on then off and indicating means upon the occurrence of the condition initiating indication.

25. Apparatus as recited in claim 20 wherein the isolation means is a transformer having the detected voltage applied to the primary winding thereof thereby inducing the isolated electrical signal on the inductively coupled secondary winding thereof.

26. Apparatus as recited in claim 20 wherein the voltage detection means is an operational amplifier having a high input impedance that provides an operational amplifier output that is the detected voltage signal.

27. Apparatus as recited in claim 20 wherein the ratio of magnitudes of the first resistance to the second resistance is 10 to 1.

28. Apparatus as recited in claim 20 wherein one of the predetermined path resistance set points is adjustable.

* * * * *